(12) United States Patent
Murgita (10) Patent No.: US 6,627,440 B1
(45) Date of Patent: Sep. 30, 2003

(54) RECOMBINANT HUMAN ALPHA-FETOPROTEIN AS A CELL PROLIFERATIVE AGENT

(75) Inventor: Robert A. Murgita, Montreal (CA)

(73) Assignee: Martinex R & D Inc., Montreal (CA)

( * ) Notice: Subject to any disclaimer, the term of this patent is extended or adjusted under 35 U.S.C. 154(b) by 0 days.

(21) Appl. No.: 09/187,978

(22) Filed: Nov. 6, 1998

Related U.S. Application Data (62) Division of application No. 08/879,469, filed on Jun. 20, 1997, which is a continuation of application No. 08/377,316, filed on Jan. 24, 1995, now abandoned.

(51) Int. Cl.$^7$ .................................................. C12N 5/00

(52) U.S. Cl. ........................ 435/404; 435/325; 435/405

(58) Field of Search ................................ 435/325, 404, 435/405

(56) References Cited

U.S. PATENT DOCUMENTS

| | | | |
|---|---|---|---|
| 4,391,912 A | * | 7/1983 | Yoshida et al. |
| 4,692,332 A | | 9/1987 | McMichael |
| 4,877,610 A | | 10/1989 | McMichael |
| 4,966,753 A | | 10/1990 | McMichael |
| 4,970,071 A | | 11/1990 | McMichael |
| 5,130,415 A | * | 7/1992 | Tecce et al. |
| 5,206,153 A | * | 4/1993 | Tamaoki et al. |
| 5,328,844 A | * | 7/1994 | Moore |

FOREIGN PATENT DOCUMENTS

| | | |
|---|---|---|
| EP | 0 001 812 A1 | 5/1979 |
| JP | 20058666 | 1/1990 |
| WO | WO 86/04241 | 7/1986 |
| WO | WO 93/05774 | 4/1993 |
| WO | WO 94/10199 | 5/1994 |

OTHER PUBLICATIONS

Rudinger, in *Peptide Hormones*, J.A. Parsons, ed., University Park Press, Baltimore, 1976, pp. 1–6.*

Abramsky et al., Alpha–fetoprotein Suppresses Experimental Allergic Encephalomyelitis, Journal of Neuroimmunology 2:1–7 (1982).

Abramsky et al., Annals New York Academy of Sciences, pp. 108–115 (1983).

Aoyagi et al., "Differential Reactivity of α–Fetoprotein with Lectins and Evaluation of Its Usefulness in the Diagnosis of Hepatocellular Carcinoma", Gann 75:809–815 (1984).

Biddle et al., "Specific cytoplasmic alpha–fetoprotein binding protein in MCF–7 human breast cancer cells and primary breast cancer tissue," Breast Cancer Research and Treatment 10:279–286 (1987).

Boismenu et al., "Expression of Domains of Mouse Alpha–Fetoprotein in *Escherichia Coli*," Life Sciences 43:673–681 (1988).

Brenner et al., "Influence of alpha–fetoprotein on the in vitro and in vivo immune response to acetylcholine receptor," Annals New York Academy of Sciences 377:208–221 (1981).

Brenner et al., "Inhibitory effect of α–fetoprotein on the binding of myasthenia gravis antibody to acetylcholine receptor," Proc. Natl. Acad. Sci. USA 77:3635–3639 (1980).

Brenner et al., "Immunosuppression of Experimental Autoimmune Myasthenia Gravis by Alpha–Fetoprotein Rich Formation," Immunology Letters 3:163–167 (1981).

Buamah et al., "Serum alpha fetoprotein heterogeneity as a means of differentiating between primary hepatocellular carcinoma and hepatic secondaries," Clinica Chimica Acta. 139:313–316 (1984).

Buschman et al., "Experimental Myasthenia Gravis Induced in Mice by Passive Transfer of Human Myasthenic Immunoglobulin," Journal of Neuroimmunology, 13:315–330 (1987).

Cohen et al., "Suppression by Alpha–Fetoprotein of Murine Natural Killer Cell Activity Stimulated in Vitro and in Vivo by Interferon and Interleukin 2," Scand. J. Immunol. 23:211–223 (1986).

Dattwyler et al., "Binding of α–foetoprotein to murine T cells," Nature 256:656–657 (1975).

Gershwin et al., The Influence of α–Fetoprotein on Moloney Sarcoma Virus Oncogenesis: Evidence For Generation of Antigen Nonspecific Suppressor T Cells, The Journal of Immunology 121:2292–2297 (1978).

Glazier et al., "Graft–Versus–Host Disease in Cyclosporin A–Treated Rats After Syngeneic and Autologous Bone Marrow Reconstitution," J. Exp. Med. 158:1–8 (1983).

Goidl et al., "Studies On The Mechanisms of Alpha–Fetoprotein Induction of Immune Suppressive Activity," Developmental Immunobiology pp. 35–55 (1979).

Hamel et al., "Phenotype and Function of Bone Marrow–Derived T– and Non–T–Cells Activated In Vitro By Alpha–Fetoprotein," In: Biological Activities of Alpha–Fetoprotein (vol. 1), Mizejewski, G.J. and Jacobson, H.I (eds.), CRC Press, Inc. (Boca Raton, FL), pp. 167–177 (1987).

Heyward et al., "Early Detection Of Primary Hepatocellular Carcinoma By Screening For Alpha–Fetoprotein In High–Risk Families," The Lancet 2:1161–1162 (1983).

Hooper et al., "Human AFP Inhibits Cell Proliferation and NK–Like Cytotoxic Activity Generated in Autologous, But Not In Allogeneic Mixed Lymphocyte Reactions," In: Biological Activities of Alpha–Fetoprotein, (vol. II) Mizejewski, G.J. and Jacobson, H.I. (eds.), CRC Press, Inc. (Boca Raton, FL), pp. 183–197 (1989).

(List continued on next page.)

*Primary Examiner*—Gary Kunz
*Assistant Examiner*—Stephen Gucker
(74) *Attorney, Agent, or Firm*—Clark & Elbing LLP (57) ABSTRACT

Disclosed is a cell culture medium including recombinant human alpha-fetoprotein or a cell-stimulating fragment or analog thereof.

1 Claim, 5 Drawing Sheets

OTHER PUBLICATIONS

Hooper et al., Selective Inhibition Of Murine T–Cell Proliferation And Lymphokine–Activated Nautral Killer Cell Function By alpha–Fetoprotein, In: Biological Activities of Alpha–Fetoprotein, (vol. 1) Mizejewski, G.J. and Jacobson, H.I. (eds.), CRC Press, Inc. (Boca Raton, FL), pp. 153–165 (1987).

Hooper et al., "Regulation of Murine T–Cell Responses to Autologous Antigens by α–Fetoprotein." Cellular Immunology 63:417–425 (1981).

Hooper et al., "Suppression Of Primary And Secondary Autologous Mixed Lymphocyte Reactions By Murine Alphafetoprotein," Oncodevelopmental Biology and Medicine 3:151–160 (1982).

Hoskin et al., Analysis of Pregnancy–Associated Immunoregulatory Pathways, In: Alpha–Fetoprotein and Cogenital Disorders, Academic Press, Inc. (New York), pp. 59–78 (1985).

Hoskin et al., "In Vitro Activation of Bone Marrow–Derived T– and Non–T–Cell Subsets by α–Fetoprotein," Cellular Immunology 96:163–174 (1985).

Hoskin et al., "Specific maternal anti–fetal lymphoproliferative responses and their regulation by natural immunosuppressive factors," Clin. exp. Immunol. 76:262–267 (1989).

Innis et al., "Amplification of α–Fetoprotein Complementary DNA by Insertion into a Bacterial Plasmid," Archives of Biochemistry and Biophysics 195:128–135 (1979).

Ishiguro et al., "Serum Alpha–Fetoprotein Subfractions in Patients With Primary Hepatoma or Hepatic Metastasis of Gastric Cancer," Cancer 55:156–159 (1985).

Jacobson et al., "Inhibition of Estrogen–dependent Breast Cancer Growth by a Reaction Product of α–Fetoprotein and Estradiol," Cancer Research 50:415–420 (1990).

Jiang et al., "Role of CD8[+] T Cells In Murine Experimental Allergic Encephalomyelitis," Science 256:1213–1215 (1992).

Keller et al., "Immunosuppressive Properties of AFP: Role Of Estrogens,"In: Onco–Developmental Gene Expression Fishman, W.H. and Sell, S. (eds.), Academic Press, Inc. (New York) pp. 287–295 (1976).

Kikutani et al., "The Murine Autoimmune Diabetes Model: NOD and Related Strains," Advances in Immunology 51:285–322 (1992).

Line et al., "Medical Potential Of AFP As A Tumor Imaging Agent," In: Biological Activities of Alpha–Fetoprotein (Vol.II), Mizejewski, G.J. and Jacobson, H.I. (eds.), CRC Press, Inc. (Boca Raton, FL), pp. 139–148 (1989).

Lu et al., "α–Fetoprotein Inhibits Macrophage Expression Of Ia Antigens," The Journal of Immunology 132:1722–1727 (1984).

Masuda et al., "Selective Antitumor Effect of Thioether–Linked Immunotoxins Composed of Gelonin and Monoclonal Antibody to Alpha–Fetoprotein or Its F(ab')$_2$ Fragment," Tumor Biol. 15:175–183 (1994).

Mizejewski et al., "Alpha Fetoprotein Testing: Regulatory and Technical Considerations," Laboratory Management (1987).

Morinaga et al., "Primary structures of human α–fetoprotein and its mRNA," Proc. Natl. Acad. Sci. USA 80:4604–4608 (1983).

Moro et al., "Monoclonal Antibodies Directed against a Widespread Oncofetal Antigen: The Alpha–Fetoprotein Receptor," Tumor Biol. 14:116–130 (1993).

Murgita et al., "Selective Immunoregulatory Properties Of α–Fetoprotein," La Ricerca Clin. Lab. 9:327–342 (1979).

Murgita et al., "Regulation of Immune Functions in the Fetus and Newborn," Progress Allergy 29:54–132 (1981).

Murgita et al., "Suppression Of The Immune Response By α–Fetoprotein," The Journal of Experimental Medicine 141:440–452 (1975).

Murgita et al., Suppression Of The Immune Response By α–Fetoprotein, The Journal of Experimental Medicine 141:269–286 (1975).

Murgita et al., "Adult murine T cells activated in vitro by α–fetoprotein and naturally occurring T cells in newborn mice: Identity in function and cell surface differentiation antigens," Proc. Natl. Acad. Sci. USA 75:2897–2901 (1978).

Murgita et al., "Effects of human alpha–foetoprotein on human B and T lymphocyte proliferation in vitro," Clin. Exp. Immunol. 33:347–356 (1978).

Murgita et al., "The Effects of Mouse Alpha–Fetoprotein on T–Cell–Dependent and T–Cell–Independent Immune Responses In Vitro," Scand. J. Immunol. 5:1215–1220 (1976).

Murgita et al., "The Immunosuppressive Role of Alpha–Feto–protein During Pregnancy," Scand. J. Immunol. 5:1003–1014 (1976).

Murgita et al., "α–Fetoprotein induces suppressor T cells in vitro," Nature 267:257–258 (1977).

Murgita et al., "Characterization of murine newborn inhibitor T lymphocytes: functional and phenotype comparison with an adult T subset activated in vitro by alpha–fetoprotein," Eur. J. Immunol. 11:957–964 (1981).

Nelson et al., "Maternal–Fetal Disparity in HLA Class II Alloantigens And The Pregnancy–Induced Amelioration of Rheumatoid Arthritis," The New England Journal of Medicine 329:466–471 (1993).

Nishi et al., "Expression of Rat α–Fetoprotein cDNA in *Escherichia coli* and in Yeast," J. Biochem. 104:968–972 (1988).

O'Neill et al., "Regulation of Human Lymphocyte Activation By Alpha–Fetoprotein: Evidence For Selective Suppression Of Ia–Associated T–Cell Proliferation In Vitro," Oncodevelopmental Biology and Medicine 3:135–150 (1982).

Peck et al., "Cellular And Genetic Restrictions In The Immunoregulatory Activity Of α–Fetoprotein," The Journal of Immunology 128:1134–1140 (1982).

Peck et al., "Cellular And Genetic Restrictions In The Immunoregulatory Activity Of Alpha–Fetoprotein," The Journal of Experimental Medicine 147:667–683 (1978).

Peck et al., "Cellular And Genetic Restrictions In The Immunoregulatory Activity Of Alpha–Fetoprotein," J. Exp. Med. 148:360–372 (1978).

Sell, "Alphafetoprotein," In: Cancer Markers Diagnostic and Developmental Significance, Sell, S., (ed.), Humana Press, Clifton, NJ pp. 249–293 (1980).

Semeniuk et al., "Immunoregulation By Recombinant Alpha–Fetoproteins Produced In Eukaryotic And Prokaryotic Expression Systems," Abstract 2799, Experimental Biology 94™, Anaheim, CA (1994).

Soto et al., "Control of growth of estrogen–sensitive cells: Role for α–fetoprotein," Proc. Natl. Acad. Sci. USA 77:2804–2087 (1980).

van Oers et al., "Analytical– And Preparative–Scale Separation Of Molecular Variants of α–Fetoprotein By Anion–Exchange Chromatography On Monobead™ Resins," Journal of Chromatography 525:59–69 (1990).

van Oers et al., "Isolation And Characterization Of A Distinct Immunoregulatory Isoform Of α–Fetoprotein Produced By The Normal Fetus," J. Exp. Med. 170:811–825 (1989).

Villacampa et al., "Alpha–Fetoprotein Receptors In A Human Breast Cancer Cell Line," Biochemical and Biophysical Research Communications 122:1322–1327 (1984).

Yamamoto et al., "Expression Of Human α–Fetoprotein In Yeast," Life Sciences 46:1679–1686 (1990).

Giuliani et al., "Synthesis and characterization of a recombinant fragment of human α–fetoprotein with antigenic selectivity versus albumin," Protein Engineering 2:605–610 (1989).

* cited by examiner

Fig. 1A

```
                                                                                                    AT  (2)
                                    -19                              -10
                                    met lys trp val glu ser ile phe leu ile phe leu leu asn phe thr glu ser arg
ATTGTGCTTCCACCACTGCCAATAACAAATAACTAGCAACC ATG AAG TGG GTG GAA TCA ATT TTT TTA ATT TTC CTA AAT TTT ACT GAA TCC AGA (101)
       1                       10                          20                               30
       thr leu his arg asn glu tyr gly ile ala ser ile leu asp ser tyr ala glu ile ser leu ala asp leu ala thr ile
       ACA CTG CAT AGA AAT GAA TAT GGA ATA GCT TCC ATA CTG GAT TCT TAC CAA GAG ATA AGT CTA GCA GAT CTG GCT ACC ATA (191)
      31                          40                          50                               60
      phe phe ala gln phe val gln glu ala thr tyr lys glu val ser lys met val lys asp ala leu thr ala ile glu lys pro thr gly
      TTT TTT GCC CAG TTT GTT CAA GAA GCC ACT TAC AAG GAA GTA AGC AAA ATG GTG AAA GAT GCA TTG ACT GCA ATT GAG AAA CCC ACT GGA (281)
      61                          70                          80                               90
      asp glu gln ser ser gly cys leu glu asn gln leu pro ala phe leu glu glu leu cys his glu lys glu ile leu glu lys tyr gly
      GAT GAA CAG TCT TCA GGG TGT TTA GAA AAC CAG CCT GCC TTT CTG GAA GAA CTT TGC CAT GAG AAA GAA ATT TTG GAG AAG TAC GGA (371)
      91                          100                         110                              120
      his ser asp cys cys ser gln ser glu gly arg his asn cys phe leu ala his lys lys pro thr pro ala ser ile pro leu phe
      CAT TCA GAC TGC TGC AGC CAA AGT GAA GAG AGA CAT AAC TGT TTT CTT GCA CAT AAG AAG CCC ACT CCA GCA TCG ATC CCA CTT TTC (461)
     121                          130                         140                              150
     gln val pro glu pro val thr ser cys glu ala tyr glu glu asp arg glu thr phe met asn lys phe ile tyr glu ile ala arg arg
     CAA GTT CCA GAA CCT GTC ACA AGC TGT GAA GCA TAT GAA GAA GAC AGG GAG ACA TTC ATG AAC AAA TTC ATT TAT GAG ATA GCA AGA AGG (551)
     151                          160                         170                              180
     his pro phe leu tyr ala ala pro thr ile leu leu trp ala ala arg tyr asp lys ile ile pro ser cys cys lys ala glu asn ala val
     CAT CCC TTC CTG TAT GCA GCA CCT ACA ATT CTT CTT TGG GCT GCC CGC TAT GAC AAA ATA ATT CCA TCT TGC TGC AAA GCT GAA AAT GCA GTT (641)
     181                          190                         200                              210
     glu cys phe gln thr lys ala ala thr val thr lys glu leu arg glu ser ser leu leu asn gln his ala cys ala val met lys asn
     GAA TGC TTC CAA ACA AAG GCA GCA ACA GTT ACA AAG GAA TTA AGA GAA AGC AGC TTG TTA AAT CAA CAT GCA TGT GCA GTA ATG AAA AAT (731)
```

```
211                 220                 230                 240
phe gly thr arg thr phe gln ala ile thr val thr lys phe thr gln lys leu ser gln lys phe thr val asn phe thr glu ile gln lys leu val
TTT GGG ACC CGA ACT TTC CAA GCC ATA ACT GTT ACT AAA TTT ACT CAG AAG CTG AGT CAG AAA TTT AAT TTT ACT GAA ATC CAG AAA CTA GTC (821)

241                 250                 260                 270
leu asp val ala his val his glu his cys cys arg gly asp val leu asp cys leu gln asp gly glu lys ile met ser tyr ile cys
CTG GAT GTG GCC CAT GTA CAT GAG CAC TGT TGC AGA GGA GAT GTG CTG GAT TGT CTG CAG GAT GGG GAA AAA ATC ATG TCC TAC ATA TGT (911)

271                 280                 290                 300
ser gln asp thr leu ser asn lys ile thr glu cys cys lys leu thr thr leu glu arg gly gln cys ile ile his ala glu asn
TCT CAA GAC ACT CTG TCA AAC AAA ATA ACA GAA TGC TGC AAA CTG ACC ACG CTG GAA CTG AGA CGT GGT CAA TGT ATA ATT CAT GCA GAA AAT(1001)

301                 310                 320                 330
asp glu lys pro glu gly leu ser pro asn leu asn arg phe leu gly asp arg asp phe ser ser gly glu lys asn ile
GAT GAA AAA CCT GAA GGT CTA TCT CCA AAT CTA AAC AGG TTT TTA GGA GAT AGA GAT TTT TCT TCA GGA GAA AAA AAT ATC(1091)

331                 340                 350                 360
phe leu ala ser phe val his glu tyr ser arg arg his pro gln leu ala val ser val ile leu arg val ala lys gly tyr gln glu
TTC TTG GCA AGT TTT GTT CAT GAA TAT TCA AGA AGA CAT CCT CAG CTT GCT GTC TCA ATT CTA AGA GTT GCT AAA GGA TAC CAG GAG(1181)

361                 370                 380                 390
leu leu glu lys cys phe gln thr glu asn pro leu glu cys gln asp lys gly glu glu leu gln lys tyr ile gln glu ser gln
TTA TTG GAG AAG TGT TTC CAG ACT GAA AAC CCT CTT GAA TGC CAA GAT AAA GGA GAA GAA TTA CAG AAA TAC ATC CAG GAG AGC CAA(1271)

391                 400                 410                 420
ala leu ala lys ser cys gly leu phe gln lys leu gly tyr tyr leu gln asn ala phe leu val ala tyr thr lys lys ala
GCA TTG GCA AAG TGT GGC CTC TTC CAG AAA CTA GGA GAA TAT TAC TTA CAA AAT GCG TTT CTC GTT GCT TAC ACA AAG AAA GCC(1361)

421                 430                 440                 450
pro gln leu thr ser ser glu leu met ala ile thr arg lys met ala ala thr ala ala thr cys cys gln leu ser glu asp lys leu
CCC CAG CTG ACC TCG TCG GAG CTG ATG GCC ATC ACC AGA AAA ATG GCA GCA ACA GCA GCC ACT TGT TGC CAA CTC AGT GAG GAC AAA CTA(1451)
```

Fig. 1B

```
451
leu ala cys gly glu gly ala ala asp ile ile ile gly his leu cys ile arg his glu met thr pro val asn pro gly val gly gln
TTG GCC TGT GGC GAG GGA GCG GCT GAC ATT ATC ATT ATC GGA CAC TTA TGT ATC AGA CAT GAA ATG ACT CCA GTA AAC CCT GGT GTT GGC CAG(1541)

481
cys cys thr ser ser tyr ala asn arg arg pro cys phe ser ser leu val val asp glu thr tyr val pro pro ala phe ser asp
TGC TGC ACT TCT TCA TAT GCC AAC AGG AGG CCA TGC TTC AGC TCC TTG GTG GTG GAT GAA ACA TAT GTC CCT CCT GCA TTC TCT GAT GAC(1631)

511
lys phe ile phe his lys asp leu cys gln ala gln gly val ala leu gln thr met lys gln glu phe leu ile asn leu val lys gln
AAG TTC ATT TTC CAT AAG GAT CTG TGC CAA GCT CAG GGT GTA GCG CTG CAA ACG ATG AAG CAA GAG TTT CTC ATT AAC CTT GTG AAG CAA(1721)

541
lys pro gln ile thr glu glu gln leu glu ala ala val ile ala asp phe ser gly leu leu glu lys cys gln gly gln glu gln glu
AAG CCA CAA ATA ACA GAG GAA CAA CTT GAG GCT GTC ATT GCA GAT TTC TCA GGC CTG TTG GAG AAA TGC CAA GGC CAG GAA CAG GAA(1811)

571
val cys phe ala glu glu gly gln lys leu ile ser lys thr arg ala ala leu gly val ter
GTC TGC TTT GCT GAA GAG GGA CAA AAA CTG ATT TCA AAA ACT CGT GCT GCT TTG GGA GTT TAA    ATTACTTCAGGGGAAGAAGAAGACAAAACGAGTCT(1908)

TTCATTCGGTGTGAACTTTCTCTCTTAATTTAACTGATTAACACTTTTGTGAATTAATGAAATGATAAGACTTTTATGTGAGATTTCCTTATCACAGAAATAAAATATCTCCAAA(2027)
```

RECOMBINANT HUMAN ALPHA-FETOPROTEIN AS A CELL PROLIFERATIVE AGENT

CROSS REFERENCE TO RELATED APPLICATIONS

This application is a divisional of and claims priority from U.S. application Ser. No. 08/879,469, filed Jun. 20, 1997, which is a File Wrapper Continuation of Ser. No. 08/377,316, filed Jan. 24, 1995, now abandoned.

BACKGROUND OF THE INVENTION

This invention relates to cell growth and cell culture.

Mammalian alpha-fetoprotein (AFP) is a 70,000-Da glycoprotein of primarily yolk sac and hepatic origin which is present in fetal blood in milligram amounts during perinatal life. At birth serum AFP levels begin a gradual decline to the low nanogram amounts normally found in the adult. Chemical analysis has shown that AFP molecules are composed of single polypeptide chains containing about 4% carbohydrate.

SUMMARY OF THE INVENTION

I have discovered that unglycosylated recombinant human alpha-fetoprotein made in a prokaryote (e.g., *E. coli*) is a cell proliferative agent, e.g., promotes the growth of bone marrow in vitro.

In general, the invention features a cell culture medium including recombinant human alpha-fetoprotein or a cell-stimulating fragment or analog thereof. Preferably, such recombinant human alpha-fetoprotein is produced in a prokaryotic cell (*E. coli*) and is unglycosylated.

Accordingly, the invention features a method of cell culture, said method including (a) providing a cell culture medium including recombinant human alpha-fetoprotein; (b) providing a cell; (c) and growing the cell in the medium, where the cell proliferates, and is maintained. Preferably, the cell is a mammalian cell. Examples of such mammalian cells include bone marrow cells (e.g., a T cells, a natural killer cell, a lymphocyte, etc.), hybridomas or a genetically-engineered cell line. Examples of other cells include hematopoietic cells such as stem cells, blast cells, progenitor cells (e.g., erythroid progenitor cells such as burst-forming units and colony-forming units), myeloblasts, macrophages, monocytes, macrophages, lymphocytes, T-lymphocytes, B-lymphocytes, eosinophils, basophils, tissue mast cells, megarkaryocytes (see e.g., *Best and Taylor's Physiological Basis of Medical Practice*, John B. West, ed., Williams & Wilkins, Baltimore). In other preferred embodiments the method involves ex vivo cell culture.

In another aspect, the invention features a method for inhibiting myelotoxcity in a mammal (e.g., a human patient) involving administering to the mammal a therapeutically effective amount of recombinant human alpha-fetoprotein or a myelotoxic-inhibiting analog or fragment thereof. Preferably, the recombinant human alpha-fetoprotein is produced in a prokaryotic cell (*E. coli*) and is unglycosylated.

In another aspect, the invention features a method of inhibiting suppression of bone marrow cell proliferation in a mammal, the method involving administering to the mammal an effective amount of recombinant alpha-fetoprotein or an anti-suppressive fragment or analog thereof. Preferably, the recombinant human alpha-fetoprotein is produced in a prokaryotic cell (e.g., *E. coli*) and is unglycosylated.

In another aspect, the invention features a method of promoting bone marrow cell proliferation in a mammal, involving administering to the mammal an effective amount of recombinant human alpha-fetoprotein or a cell-stimulating fragment or analog thereof. Preferably, the recombinant human alpha-fetoprotein is produced in a prokaryotic cell (e.g., *E. coli*) and is unglycosylated.

In another aspect, the invention features a method of preventing bone marrow cell transplantation rejection in a mammal, involving administering to the mammal an effective amount of recombinant human alpha-fetoprotein or an anti-rejection fragment or analog thereof. Preferably, the recombinant human alpha-fetoprotein is produced in a prokaryotic cell (e.g., *E. coli*) and is unglycosylated.

By "cell-stimulating" is meant increasing cell proliferation, increasing cell division, promoting cell differentiation and/or development, or promoting cell longevity.

By "therapeutically effective amount" is meant a dose of unglycosylated recombinant human alpha-fetoprotein or an cell-stimulating fragment or analog thereof capable of stimulating the proliferation of a cell.

By "recombinant human alpha-fetoprotein" is meant a polypeptide having substantially the same amino acid sequence as the protein encoded by the human alpha-fetoprotein gene (FIG. 1, SEQ ID NO: 1) as described by Morinaga et al., *Proc. Natl. Acad. Sci., USA* 80: 4604 (1983). The method of producing recombinant human alpha-fetoprotein in a prokaryotic cell is described in U.S. Pat. No. 5,384,250.

By "myelotoxic-inhibiting" is meant inhibiting myeloablation.

According to the invention, administration of recombinant human alpha-fetoprotein ("rHuAFP") (or a fragment or analog thereof) can be an effective means for promoting and boosting cell growth in vitro, ex vivo, or in vivo. Administration of such rHuAFP can also be an effective means of preventing or treating or ameliorating myleotoxcemia in a mammal.

The use of rHuAFP is especially advantageous since there are no known adverse side effects related to human alpha-fetoprotein and it is believed that relatively high doses can be safely administered. Furthermore, the use of rHuAFP as a principal component of tissue culture media is advantageous since there is little potential for contamination with pathogens.

Other features and advantages of the invention will be apparent from the following detailed description, and from the claims.

DETAILED DESCRIPTION

The drawing will first be described.

Drawings

FIG. 1 is the nucleotide sequence (SEQ ID NO: 1) and deduced amino acid sequence (SEQ ID NO: 3) of the cDNA encoding human alpha-fetoprotein.

PRODUCTION OF RECOMBINANT HUMAN ALOHA-FETOPROTEIN

As summarized above, the invention includes therapies for promoting cell proliferation and for the prevention and treatment of a myelotoxic condition involving administering recombinant human alpha-fetoprotein ("rHuAFP") or fragments or analogs thereof. Methods for producing such rHuAFP in a prokaryotic cell are described in U.S. Pat. No. 5,384,250. Methods for producing rHuAFP fragments and analogs will now be discussed in greater detail.

Fragments and Analogs

The invention includes biologically active fragments of rHuAFP. A biologically active fragment of rHuAFP is one that possesses at least one of the following activities: (a) directs a specific interaction with a target cell, e.g., binds to a cell expressing a receptor which is recognized by rHuAFP (e.g., the membrane of a bone marrow cell); or (b) stimulates, increases, expands or otherwise causes the proliferation of a cell (e.g., binds to a cell surface receptor to impart an proliferative or stimulating-signal). The ability of rHuAFP fragments or analogs to bind to a receptor which is recognized by rHuAFP can be tested using any standard binding assay known in the art. Biological activity of a rHuAFP fragment or analog can also be tested according to standard methods, e.g., those described herein.

In general, fragments of rHuAFP are produced according to the techniques of polypeptide expression and purification described in U.S. Pat. No. 5,384,250. For example, suitable fragments of rHuAFP can be produced by transformation of a suitable host bacterial cell with part of an HuAFP-encoding cDNA fragment (e.g., the cDNA described above) in a suitable expression vehicle. Alternatively, such fragments can be generated by standard techniques of PCR and cloned into the expression vectors (supra). Accordingly, once a fragment of rHuAFP is expressed, it may be isolated by various chromatographic and/or immunological methods known in the art. Lysis and fractionation of rHuAFP-containing cells prior to affinity chromatography may be performed by standard methods. Once isolated, the recombinant protein can, if desired, be further purified, e.g., by high performance liquid chromatography (see, e.g., Fisher, *Laboratory Techniques In Biochemistry And Molecular Biology*, Work and Burdon, eds., Elsevier, 1980).

A rHuAFP fragment may also be expressed as a fusion protein with maltose binding protein produced in *E. coli*. Using the maltose binding protein Fusion and purification system (New England Biolabs), the cloned human cDNA sequence can be inserted downstream and in frame of the gene encoding maltose binding protein (malE), and the malE fusion protein can then be overexpressed. In the absence of convenient restriction sites in the human cDNA sequence, PCR can be used to introduce restriction sites compatible with the vector at the 5' and 3' end of the cDNA fragment to facilitate insertion of the cDNA fragment into the vector.

Following expression of the fusion protein, it can be purified by affinity chromatography. For example, the fusion protein can be purified by virtue of the ability of the maltose binding protein portion of the fusion protein to bind to amylose immobilized on a column.

To facilitate protein purification, the pMalE plasmid contains a factor Xa cleavage site upstream of the site into which the cDNA is inserted into the vector. Thus, the fusion protein purified as described above can then be cleaved with factor Xa to separate the maltose binding protein from a fragment of the recombinant human cDNA gene product. The cleavage products can be subjected to further chromatography to purify rHuAFP from the maltose binding protein. Alternatively, a fragment of rHuAFP may be expressed as a fusion protein containing a polyhistidine tag can be produced. Such an alpha-fetoprotein fusion protein may then be isolated by binding of the polyhistidine tag to an affinity column having a nickel moiety which binds the polyhistidine region with high affinity. The fusion protein may then be eluted by shifting the pH within the affinity column. The rHuAFP can be released from the polyhistidine sequences present in the resultant fusion protein by cleavage of the fusion protein with specific proteases.

Recombinant HuAFP fragment expression products (e.g., produced by any of the prokaryotic systems described in U.S. Pat. No. 5,384,250 may be assayed by immunological procedures, such as Western blot, immunoprecipitation analysis of recombinant cell extracts, or immunofluorescence (using, e.g., the methods described in Ausubel et al., *Current Protocols In Molecular Biology*, Greene Publishing Associates and Wiley Interscience (John Wiley & Sons), New York, 1994).

Once a fragment of rHuAFP is expressed, it is isolated using the methods described supra. Once isolated, the fragment of rHuAFP can, if desired, be further purified by using the techniques described supra. Fragments can also be produced by chemical synthesis (e.g., by the methods described in *Solid Phase Peptide Synthesis*, 2nd ed., 1984, The Pierce Chemical Co., Rockford, Ill.).

The ability of a candidate rHuAFP fragment to exhibit a biological activity of alpha-fetoprotein is assessed by methods known to those skilled in the art (e.g., those described herein).

The purified recombinant gene product or fragment thereof can then be used to raise polyclonal or monoclonal antibodies against the human recombinant alpha-fetoprotein using well-known methods (see Coligan et al., eds., current *Protocols in Immunology*, 1992, Greene Publishing Associates and Wiley-Interscience). To generate monoclonal antibodies, a mouse can be immunized with the recombinant protein, and antibody-secreting B cells isolated and immortalized with a non-secretory myeloma cell fusion partner. Hybridomas are then screened for production of recombinant human alpha-fetoprotein (or a fragment or analog thereof)-specific antibodies and cloned to obtain a homogenous cell population which produces monoclonal antibodies.

As used herein, the term "fragment," as applied to a rHuAFP polypeptide, is preferably at least 20 contiguous amino acids, preferably at least 50 contiguous amino acids, more preferably at least 100 contiguous amino acids, and most preferably at least 200 to 400 or more contiguous amino acids in length. Fragments of rHuAFP molecules can be generated by methods known to those skilled in the art, e.g., proteolytic cleavage or expression of recombinant peptides, or may result from normal protein processing (e.g., removal of amino acids from nascent polypeptide that are not required for biological activity).

Recombinant HuAFP fragments of interest include, but are not limited to, Domain I (amino acids 1 (Thr)—197 (Ser), see FIG. 1, SEQ ID NO: 3), Domain II (amino acids 198 (Ser)—389 (Ser), see FIG. 1, SEQ ID NO: 4), Domain III (amino acids 390 (Gln)—590 (Val), see FIG. 1, SEQ ID NO: 6), Domain I+II (amino acids 1 (Thr)—389 (Ser), see FIG. 1, SEQ ID NO: 6) Domain II+III (amino acids 198 (Ser)—590 (Val), see FIG. 1, SEQ ID NO: 7), and rHuAFP Fragment I (amino acids 266 (Met)—590 (Val), see FIG. 1, SEQ ID NO: 8). Activity of a fragment is evaluated experimentally using conventional techniques and assays, e.g., the assays described herein.

The invention further includes analogs of full-length rHuAFP or fragments thereof. Analogs can differ from rHuAFP by amino acid sequence differences, or by modifications (e.g., post-translational modifications) which do not affect sequence, or by both. Analogs of the invention will generally exhibit at least 80%, more preferably 85%, and most preferably 90% or even 99% amino acid identity with all or part of a rHuAFP amino acid sequence. Modifications (which do not normally alter primary sequence) include in vivo, or in vitro chemical derivatization of polypeptides, e.g., acetylation, or carboxylation; such modifications may occur during polypeptide synthesis or processing or following treatment with isolated modifying enzymes. Analogs can also differ from the naturally occurring rHuAFP by alterations in primary sequence, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. These include genetic variants, both natural and induced (for example, resulting from random mutagenesis by irradiation or exposure to ethanemethylsulfate or by site-specific mutagenesis as described in Sambrook et al., *Molecular Cloning: A Laboratory Manual*, 2nd ed., Cold Spring Harbor Press, 1989, or Ausubel et al., supra). Also included are cyclized peptide molecules and analogs which contain residues other than L-amino acids, e.g., D-amino acids or non-naturally occurring or synthetic amino acids, e.g., β or γ amino acids, or L-amino acids with non-natural side chains (see e.g., Noren et al., *Science* 244:182, 1989). Methods for site-specific incorporation of non-natural amino acids into the protein backbone of proteins is described, e.g., in Ellman et al., *Science* 255:197, 1992. Also included are chemically synthesized polypeptides or peptides with modified peptide bonds (e.g., non-peptide bonds as described in U.S. Pat. No. 4,897,445 and U.S. Pat. No. 5,059,653) or modified side chains to obtain the desired pharmaceutical properties as described herein. Useful mutants and analogs are identified using conventional methods, e.g., those described herein.

Sninsky, and Thomas J. White, eds., Academic Press, Inc., New York, 1990, and Ausubel et. al., supra).

The following six rHuAFP fragments were prepared to evaluate their biological activity (e.g., according to the methods disclosed herein):

| | |
|---|---|
| Domain I | Amino acids 1 (Thr) - 197 (Ser), (FIG. 1, SEQ ID NO: 3) |
| Domain II | Amino acids 198 (Ser) - 389 (Ser), (FIG. 1, SEQ ID NO: 4) |
| Domain III | Amino acids 390 (Gln) - 590 (Val), (FIG. 1, SEQ ID NO: 5) |
| Domain I + II | Amino acids 1 (Thr) - 389 (Ser), (FIG. 1, SEQ ID NO: 6) |
| Domain II + III | Amino acids 198 (Ser) - 590 (Val), (FIG. 1, SEQ ID NO: 7) |
| rHuAFP Fragment I | Amino acids 266 (Met) - 590 (Val), (FIG. 1, SEQ ID NO: 8) |

Amino acid sequences were deduced from those shown for human alpha-fetoprotein (1 (Thr)—590 (Val), SEQ ID NO: 2) in FIG. 1. Fragments of rHuAFP designated Domain I, Domain II, Domain III, Domain I+II, Domain II+III and rHuAFP Fragment I were synthesized using standard PCR reaction conditions in 100 μL reactions containing 34 μL H$_2$O, 10 μL 10× reaction buffer, 20 μL 1 mM dNTP, 2 μL DNA template (HuAFP cloned in pI18), appropriate 5' and 3' oligonucleotide primers (10 μL 10 pmol/μL 5' primer, 10 μL 10 pmol/μL 3' primer), 1 μL glycerol, 10 μL DMSO, and 1 μL Pfu polymerase. (Stratagene, LaJolla, Calif.). Primers used for PCR amplifications were:

| | | |
|---|---|---|
| DomI25 | 5'-AAAAAAGGTACCACACTGCATAGAAATGAA-3' | (SEQ ID NO: 9) |
| DomI3 | 5'-AAAAAAGGATCCTTAGCTTTCTCTTAATTCTTT-3' | (SEQ ID NO: 10) |
| DomII5 | 5'-AAAAAAATCGATATGAGCTTGTTAAATCAACAT-3' | (SEQ ID NO: 11) |
| DomII3 | 5'-AAAAAAGGATCCTTAGCTCTCCTGGATGTATTT-3' | (SEQ ID NO: 12) |
| DomIII5 | 5'-AAAAAAATCGATATGCAAGCATTGGCAAAGCGA-3' | (SEQ ID NO: 13) |
| DomIII3 | 5'-AAAAAAGGATCCTTAAACTCCCAAAGCAGCACG-3' | (SEQ ID NO: 14) |
| 5'-rHuAFP Fragment I | 5'-AAAAAAATCGATATGTCCTACATATGTTCTCAA-3' | (SEQ ID NO: 15) |

The cloning, expression, isolation and characterization of exemplary rHuAFP fragments now follows. These examples are provided to illustrate, not limit, the invention.

EXPERIMENTAL

Materials and Methods
Polymerase Chain Reaction (PCR) rHuAFP Fragments

Plasmid constructs encoding fragments of human alpha-fetoprotein were prepared using polymerase chain reaction (PCR) techniques known to those skilled in the art of molecular biology, using oligonucleotide primers designed to amplify specific portions of the human alpha-fetoprotein gene (see e.g., *PCR Technology*, H. A. Erlich, ed., Stockton Press, New York, 1989; *PCR Protocols: A Guide to Methods and Applications*, M. A. Innis, David H. Gelfand, John J.

Accordingly, primer pairs DomI25 and DomI3, DomII5 and DomII3, DomIII15 and DomIII3, 5'rHuAFP Fragment I and DomIII3, DomI25 and DomII3, and DomII5 and DomIII3 were used to isolate cDNA sequences of Domain I, Domain II, Domain III, rHuAFP Fragment I, Domain I+II, and Domain II+III, respectively, of rHuAFP. Annealing, extension, and denaturation temperatures were 50° C., 72° C., and 94° C., respectively, for 30 cycles. PCR products were purified according to standard methods. Purified PCR products encoding Domain I and Domain I+II were digested individually with KpnI and BamHI and cloned separately into KpnI/BamHI-treated pTrp4. Purified PCR products encoding Domain II, Domain III, Domain II+III, and rHuAFP Fragment I were digested individually with Bsp106I and BamHI and were cloned separately into Bsp106I/BamHI-treated pTrp4. Each plasmid construct was subsequently transformed into competent *E. coli* cells. Since the expression product will begin with the amino acid sequence encoded by the translation start signal methionine, it is expected that such signal will be removed, or in any event, not affect the bioactivity of the ultimate expression product.

RESULTS

Expression and Purification

Figure 2:
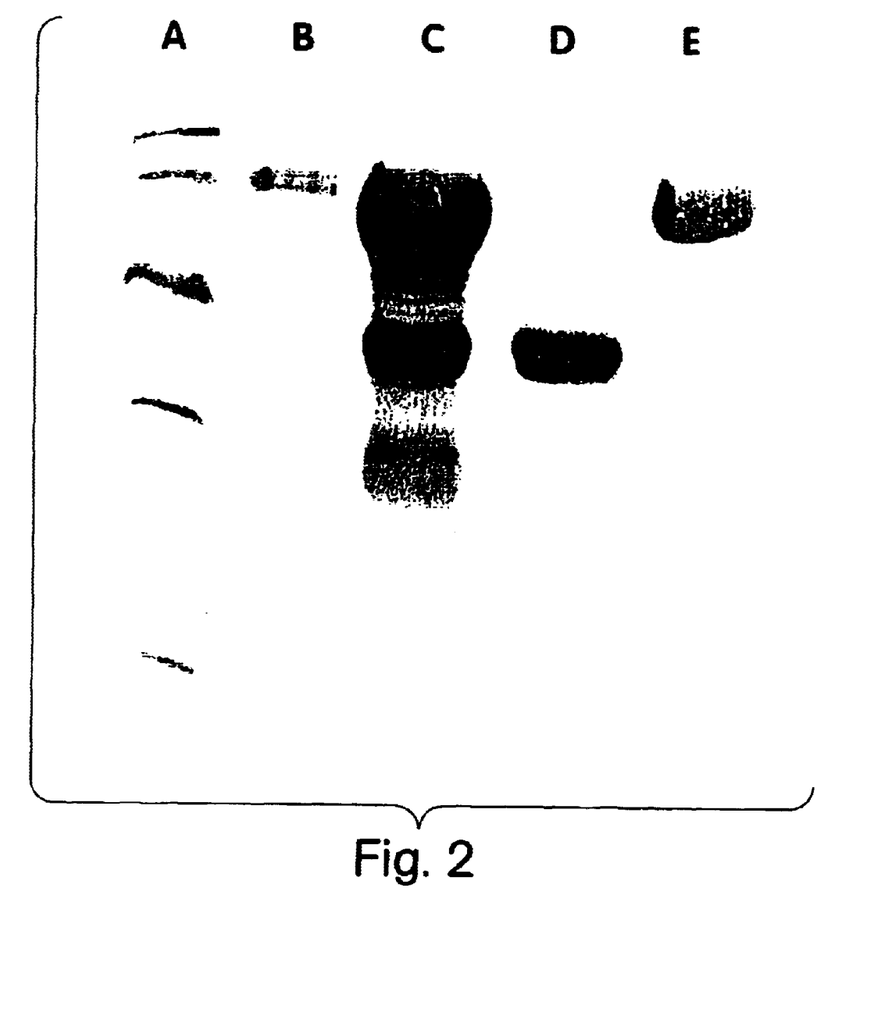
FIG. 2 is the SDS-PAGE analysis of rHuAFP Fragment I (SEQ ID NO: 2) (Lane A, MW marker; Lane B, natural human alpha-fetoprotein (AFP); Lane C, unpurified rHuAFP; Lane D, rHuAFP Fragment I, and. Lane E, rHuAFP (amino acids.1–590 of FIG. 1, SEQ ID NO: 2).

*E. coli* containing the expression plasmid encoding rHuAFP Fragment I was cultured and purified. FIG. 2 (lane D) shows the SDS-PAGE profile of the purified rHuAFP Fragment I. N-terminal amino-acid sequence analysis showed that rHuAFP Fragment I possessed the amino acid sequence $Ser_{267}$-Tyr-Ile-Cys-Ser-Gln-Gln-Asp-$Thr_{275}$ (SEQ ID NO: 16) which corresponds to the expected N-terminal amino acid sequence of rHuAFP Fragment I (see FIG. 1, SEQ ID NO: 8) where the initiating methionine is cleaved intracellularly.

Cell Culture Media

The invention provides a media containing rHuAFP (or a fragment or analog thereof) for cell culture. While media of the invention generally does not require the use of serum (e.g., fetal bovine serum, calf serum, horse serum, normal mouse serum, human serum, porcine serum, rabbit serum etc.), since such rHuAFP is intended to replace or supplement the use of serum, those skilled in the art will understand and recognize that serum can be added if desired. Media formulations are generally prepared according to methods known in the art. Accordingly, any standard medium, e.g., RMPI-1630 Medium, CMRL Medium, Dulbecco's Modified Eagle Medium (D-MEM), Fischer's Medium, Iscove's Modified Dulbecco's Medium, McCoy's Medium, Minimum Essential Medium, NCTC Medium, and the like can be formulated with rHuAFP (or a fragment or analog thereof) at the desired effective concentration. If desired, media supplements, e.g., salt solutions (e.g., Hank's Balanced Salt Solution or Earle's Balanced Salt Solution), antibiotics, nucleic acids, amino acids, carbohydrates, and vitamins are added according to known methods. If desired, growth factors, colony-stimulating factors, cytokines and the like can also be added to media according to standard methods. For example, media of the invention can contain any of the following substances, alone or in combination, with rHuAFP (or a fragment or analog thereof): erythropoietin, granulocyte/macrophage colony-stimulating factor (GM-CSF), granulocyte colony-stimulating factor (G-CSF), macrophage colony-stimulating factor (M-CSF), an interleukin (e.g., IL-1, IL-2, IL-3, IL-4, IL-5, etc.), insulin-growth factor (IGF), transferrin, albumin, and stem-cell growth factor (SCF). Media of the invention are useful for culturing a variety of eukaryotic cells, e.g., mammalian cells, yeast cells, amphibian cells, and insect cells. Media can also be used for culturing any tissue or organ. Such media can also be used in a variety of culture conditions and for a variety of biological applications. Examples of such culture conditions include, without limitation, bioreactors (e.g., continuous or hollow fiber bioreactors), cell-suspension. cultures, semisolid cultures, liquid cultures, and long-term cell suspension cultures. Media of the invention are also useful for industrial applications, e.g., culturing hybridoma cells, genetically-engineered mammalian cells, tissues or organs.

Recombinant Human Alpha-fetoprotein as a cell-proliferative Agent

Cell growth-promoting attributes of rHuAFP (or a fragment or analog thereof) is evaluated by any standard assay for analysis of cell proliferation in vitro and in vivo. As discussed infra, the art provides animal systems for in vivo testing of cell growth promoting or boosting characteristics of rHuAFP (or a fragment or analog thereof). Furthermore, a wide variety of in vitro systems are also available for testing growth-promoting or growth-boosting aspects of rHuAFP (or a fragment or analog thereof).

Any cell that proliferates in response to rHuAFP (or a fragment or analog thereof) can be identified according to standard methods known in the art. For example, proliferation of a cell (e.g., a bone marrow cell) can be monitored by culturing in a liquid media containing the test compound, either alone or in combination with other growth factors, added artificially to a serum-free or serum-based medium. Alternatively, such bone marrow cells can be cultured in a semisolid matrix of dilute, agar or methylcellulose, and the test compound, alone or in combination with other growth factors, can be added artificially to a serum-free or serum-reduced medium. In the semisolid matrix the progeny of an isolated precursor cell, proliferating in response to rHuAFP or a fragment or analog thereof, remain together as a distinguishable colony. For example, a bone marrow cell may be seen to give rise to a clone of a plurality of bone marrow cells, e.g., NK cells. Such culture systems provide a facile way for assaying whether a cell responds to rHuAFP (a fragment or analog thereof) either alone or in combination with other growth factors.

If desired, identification and separation of expanded sub-populations of cells is performed according to standard methods. For example, cells may be analyzed by fluorescence-activated cell sorting (FACS). This procedure generally involves labelling cells with antibodies coupled to a fluorescent dye and separating the labeled cells from the unlabelled cells in a FACS, e.g., FACScan (Becton Dickson). Thus virtually any cell can be identified and separated, e.g., by analyzing the presence of cell surface antigens (see e.g., Shah et al., *J. Immunol.* 140:1861, 1988). When a population of cells is obtained, it is then analyzed biochemically or, alternatively, provides a starting population for additional cell culture, allowing the action of the cells to be evaluated under defined conditions in culture.

In one working example, the effect of rHuAFP (or a fragment or analog thereof) on the growth of human bone marrow cells is examined as follows. In general, human bone marrow samples are obtained according to standard procedures after informed consent. For example, bone marrow is obtained from the iliac crest of a healthy donor and the marrow cells are diluted in phosphate-buffered saline at room temperature. Cells are then washed and cultured in an appropriate growth medium. For example, cultures can be set up by inoculating bone marrow cells in 20–30 ml of McCoy's medium containing 50 U/ml penicillin, 50 U/ml streptomycin and 2 mM L-glutamine. Cultures are incubated in the presence or absence of the test compound alone, or in combination with other growth factors, e.g., transferrin or GM-CSF. The cultures are subsequently incubated at 37° C. in a humidified atmosphere containing 5% $CO_2$, 5% $O_2$, and 90% $N_2$ for the desired time period. Cell proliferation assays are performed according to standard methods. For example, replicate samples cultured in the presence and absence of the test compound are analyzed by pulsing the cells with 1–2 $\mu$Ci of $^3$HTdR. After an incubation period, cultures are harvested onto glass-fiber filters and the incorporated $^3$H measured by liquid scintillation. Comparative studies between treated and control cells, e.g., cell cultured in the presence of rHuAFP versus cells cultured in the absence of rHuAFP, are used to determine the relative efficacy of the test molecule in stimulating cell proliferation. A molecule which stimulates cell proliferation is considered useful in the invention.

To evaluate the proliferative effects of rHuAFP (or a fragment or analog thereof) e.g., the effect of the test compound on hematopoiesis in vivo, the test molecule is administered to sublethally irradiated mice (or mice treated with an immunosuppressive agent such as cyclosporine or FK-506, or a chemotherapeutic agent such as 5-fluorouracil or cyclophosphamide or any other method known in the art to deplete bone marrow) and normal mice according to standard methods, e.g., intravenously or intraperitoneally, at an appropriate dosage on a daily basis. Generally, administration of the test compound to treated mice is initiated prior to and/or after treating the animal, e.g., with sublethal radiation or immunotherapy or chemotherapy. Control animals receive a placebo, e.g., human serum albumin or diluent, similarly administered as for rHuAFP or related molecules. The effect of the test molecule on hematopoiesis is monitored by standard techniques. For example, white blood cell count in peripheral blood and spleen in both treated and control animals are analyzed. Qualitative and quantitative analyses of bone marrow, e.g., lymphocytic lineage or myeloid lineage or any other cell type, can also be determined and analyzed according to conventional methods. Comparative data between treated and control animals are used to determine the relative efficacy of the test molecule in promoting cell proliferation, e.g., stimulates bone marrow cell production, mature B lymphocyte, thymocyte, or peripheral T lymphocyte cell production. A test molecule which stimulates cell proliferation is considered useful in the invention.

The following example demonstrates that unglycosylated rHuAFP stimulates the growth of bone marrow cells in vitro. This example is provided to illustrate, not limit, the invention.

EXPERIMENTAL

Materials and Methods

Animals

Adult male and female CBA/J mice were obtained from the Jackson Laboratory (Bar Harbor, Me.). All mice were bred and maintained in our animal facility. Animals used in this study were 12 to 20 weeks old.

Cultures

Bone marrow cells were collected by flushing the tibias and femurs of CBA/J mice with modified Dulbecco's phosphate-buffered saline (PBS) using a sterile syringe and 25-gauge needle. Homogenous single-cell suspensions were obtained by the repeated passage of cell mixtures through a Pasteur pipet. All cells were washed twice by centrifugation at 250 g for 10 min in PBS and then assessed for viability by trypan blue dye exclusion. A cell viability of 95% or better was recorded in all experiments. Cells were then adjusted to the desired concentration prior to use. Bone marrow cells (250,000) were cultured in 96-well round-bottom microtiter plates (Flow Laboratories, Mississauga, Ontario, Canada). The culture medium was serum-free RPMI plus 4 mM L-glutamine, 20 mM Hepes, 100 U/ml penicillin, 100 $\mu$g/ml streptomycin (GIBCO Laboratories, Burlington, Ontario, Canada), 5 $\mu$g/ml transferrin, and $5 \times 10^{-5}$ 2-mercaptoethanol (Eastman Chemicals Co., Rochester N.Y.). Cells were cultured in the presence or absence of rHuAFP at a concentration of 400 $\mu$g/ml, respectively. Total volume of all cultures was 0.2 ml. Cultures were maintained at 37° C. in 95% humidified air and 5% $CO_2$. Six hours prior to harvesting, the cultures were pulsed with 1 $\mu$Ci tritiated thymidine (NEN, sp act 77.1 Ci/mmol). Cells were then harvested on glass fiber mats (Flow Labs) with a multiple sample harvester (Skatron, Flow Labs). Water-insoluble tritiated thymidine incorporation was measured with an LKB 1215 Rackbeta II using standard liquid scintillation techniques.

rHuAFP

Recombinant HuAFP was synthesized and purified using the methods described in U.S. Pat. No. 5,384,250. Alternatively, rHuAFP can be obtained from Immtek, Inc. (Boston, Mass.).

RESULTS

Effects of rHuAFP on Bone Marrow Proliferation in Serum-free Media

Figure 3:
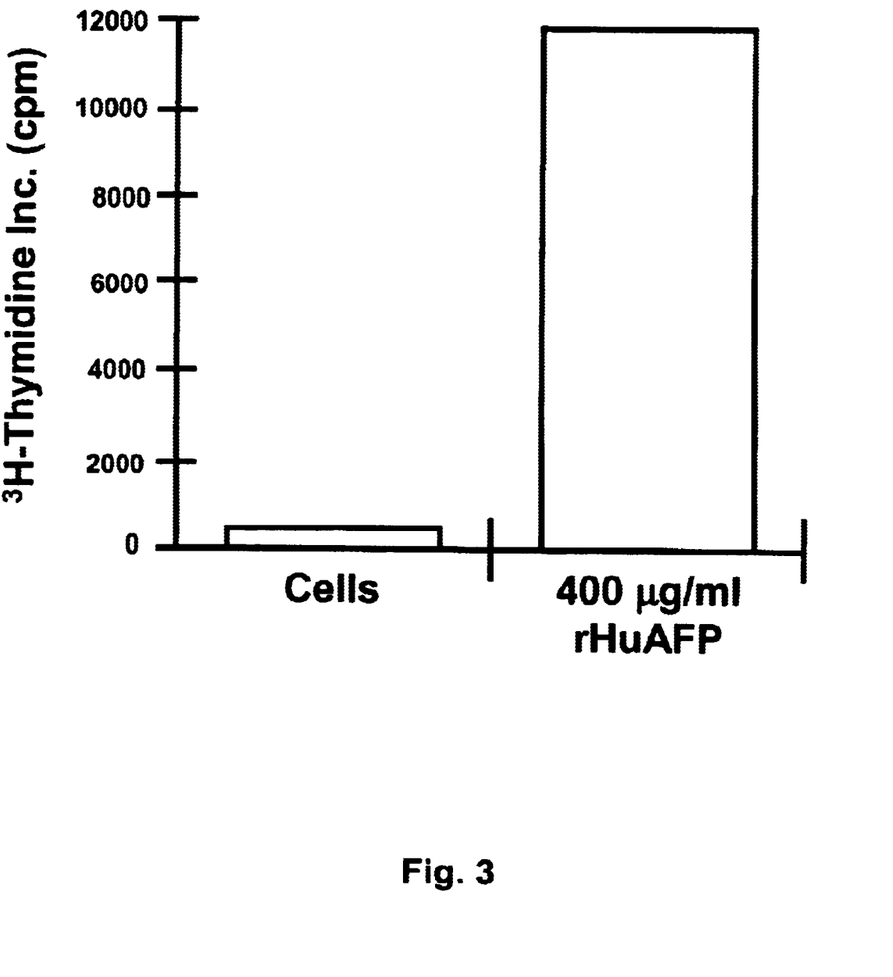
FIG. 3 is a bar graph showing murine bone marrow proliferation in serum-free RPMI medium in the presence or absence of both 400 µg/ml rHuAFP and 5 µg/ml transferrin.

The effects of purified rHuAFP on cultured murine bone marrow was evaluated in serum-free medium. In this experiment, $2.5 \times 10^5$ viable cells from bone marrow of CBA/J mice were cultured for 72 hours in serum-free RPMI media in the presence or absence of rHuAFP at a final concentration of 400 $\mu$g/ml and transferrin at a final concentration of 5 $\mu$g/ml. Data shown in FIG. 3 indicate that bone marrow cells undergo a strong proliferative response in the presence of unglycosylated rHuAFP; with a stimulation index (SI) of 35. No such proliferation was observed when bone marrow cells were cultured in the absence of rHuAFP.

Therapy

As demonstrated above, rHuAFP is effective in promoting the proliferation of cells and accordingly is useful for therapy involving the promotion of cell proliferation, e.g., proliferation of bone marrow cells, and in treatment for the prevention of side effects of immunosuppressive therapy, radiotherapy or chemotherapy, or other therapies known to depress the immune system and suppress bone marrow production, causing myelotoxicity. Accordingly, rHuAFP (or a fragment or analog thereof) is employed to treat deficiencies in hematopoietic progenitor or stem cells, or related disorders. Recombinant HuAFP (or a fragment or analog thereof) may also be employed in methods for treating cancer and other pathological states resulting in myelotoxcity, exposure to radiation or drugs, and including for example, leukopenia, bacterial and viral infections, anemia, B cell or T cell deficiencies, including immune cell or hematopoietic cell deficiency following autologous or non-autologous bone marrow transplantation. Recombinant HuAFP (or a fragment or analog thereof) may also be employed to stimulate development of megakaryocytes and natural killer cells in vitro or in vivo.

The media, compositions, and methods of the invention are also useful for treating cancers that are treated by bone marrow transplants (BMT) that involve removing bone marrow cells from the patient, maintaining these cells in an ex vivo culture while the patient is treated with radiation or chemotherapy, and then transplanting these cells back into the patient after the treatment has been completed to restore the patient's bone marrow. Accordingly, rHuAFP may be employed for BMT as a means for reconstituting bone marrow in ex vivo cell culture medium and for promoting bone marrow cell proliferation in vivo. Recombinant HuAFP (a fragment or analog thereof) is also useful for other cell therapies, e.g. cell expansion and/or gene therapy protocols, therapies requiring ex vivo cell culture. Recombinant HuAFP (a fragment or analog) is also useful in the prevention of autolocous or allogenic bone marrow transplant rejection.

Therapeutic Administration

Recombinant HuAFP (or a fragment or analog thereof) can be formulated according to known methods to prepare pharmaceutically useful compositions. Recombinant human alpha-fetoprotein, e.g., rHuAFP (or a fragment or analog thereof), is preferably administered to the patient in an amount which is effective in preventing or ameliorating the symptoms of myleotoxicity. Generally, a dosage of 0.1 ng/kg to 10 g/kg body weight is adequate. For example, treatment of human patients will be carried out using a therapeutically effective amount of rHuAFP (or a fragment or analog thereof) in a physiologically acceptable carrier. Suitable carriers and their formulation are described for example in Remington's *Pharmaceutical Sciences* by E. W. Martin. The amount of rHuAFP to be administered will vary depending upon the manner of administration, the age and body weight of the patient, and with the type of disease, and size of the patient predisposed to or suffering from the disease. Preferable routes of administration include, for example, oral, subcutaneous, intravenous, intrperitoneally, intramuscular, transdermal or intradermal injections which provide continuous, sustained levels of the drug in the patient. In other preferred routes of administration, rHuAFP can be given to a patient by injection or implantation of a slow release preparation, for example, in a slowly dissociating polymeric or crystalline form; this sort of sustained administration can follow an initial delivery of the drug by more conventional routes (for example, those described above). Alternatively, rHuAFP can be administered using an external or implantable infusion pump, thus allowing a precise degree of control over the rate of drug release, or through installation of rHuAFP in the nasal passages in a similar fashion to that used to promote absorption of insulin. As an alternative to nasal transmucosal absorption, rHuAFP can be delivered by aerosol deposition of the powder or solution into the lungs.

The therapeutic method(s) and compositions of the present invention may also include co-administration with other human growth factors. Exemplary cytokines or hematopoietins for such use include, without limitation, factors such as an interleukin (e.g., IL-1), GM-CSF, G-CSF, M-CSF, tumor necrosis factor (TNF), transferrin, and erythropoietin. Growth factors like B cell growth factor, B cell differentiation factor, or eosinophil differentiation factors may also prove useful in co-administration with rHuAFP (or a fragment or analog thereof). The dosage recited above would be adjusted to compensate for such additional components in the therapeutic composition. Progress of the treated patient can be monitored by conventional methods.

Treatment is started generally with the diagnosis or suspicion of myelotoxicity and is generally repeated on a regular or daily basis to ameliorate or prevent the progression or exacerbation of the condition. Protection or prevention from the development of a myleotoxcemic condition is also achieved by administration of rHuAFP prior to the onset of the disease. If desired, the efficacy of the treatment or protection regimens is assessed with the methods of monitoring or diagnosing patients for myelotoxcity.

The method(s) of the invention can also be used to treat non-human mammals, for example, domestic pets, or livestock.

All publications, manufacturer's instructions, patents, and patent applications mentioned in this specification are herein incorporated by reference to the same extent as if each individual publication or patent application was specifically and individually indicated to be incorporated by reference.

What is claimed is:

1. A fresh, non-spent cell culture medium substantially free of cells comprising recombinant human alpha-fetoprotein or a cell-stimulating fragment thereof, wherein said recombinant human alpha-fetoprotein is produced in *Escherichia coli.*

* * * * *

SEQUENCE LISTING

<160> NUMBER OF SEQ ID NOS: 16

<210> SEQ ID NO 1
<211> LENGTH: 2022
<212> TYPE: DNA
<213> ORGANISM: Homo sapiens

<400> SEQUENCE: 1

```
atattgtgct tccaccactg ccaataacaa aataactagc aaccatgaag tgggtggaat      60
caattttttt aattttccta ctaaatttta ctgaatccag aacactgcat agaaatgaat     120
atggaatagc ttccatattg gattcttacc aatgtactgc agagataagt ttagctgacc     180
tggctaccat attttttgcc cagtttgttc aagaagccac ttacaaggaa gtaagcaaaa     240
tggtgaaaga tgcattgact gcaattgaga aacccactgg agatgaacag tcttcagggt     300
gtttagaaaa ccagctacct gcctttctgg aagaactttg ccatgagaaa gaaattttgg     360
agaagtacgg acattcagac tgctgcagcc aaagtgaaga gggaagacat aactgttttc     420
ttgcacacaa aaagcccact gcagcatgga tcccactttt ccaagttcca gaacctgtca     480
caagctgtga agcatatgaa gaagacaggg agacattcat gaacaaattc atttatgaga     540
tagcaagaag gcatcccttc ctgtatgcac ctacaattct tctttcggct gctgggtatg     600
agaaaataat tccatcttgc tgcaaagctg aaaatgcagt tgaatgcttc caaacaaagg     660
cagcaacagt tacaaaagaa ttaagagaaa gcagcttgtt aaatcaacat gcatgtccag     720
taatgaaaaa ttttgggacc cgaactttcc aagccataac tgttactaaa ctgagtcaga     780
agtttaccaa agttaatttt actgaaatcc agaaactagt cctggatgtg gcccatgtac     840
atgagcactg ttgcagagca gatgtgctgg attgtctgca ggatgggaa aaaatcatgt     900
cctacatatg ttctcaacaa gacactctgt caaacaaaat aacagaatgc tgcaaactga     960
ccacgctgga acgtggtcaa tgtataattc atgcagaaaa tgatgaaaaa cctgaaggtc    1020
tatctccaaa tctaaacagg tttttaggag atagagattt taaccaattt tcttcagggg    1080
aaaaaaatat cttcttggca agttttgttc atgaatattc aagaagacat cctcagcttg    1140
ctgtctcagt aattctaaga gttgctaaag gataccagga gttattggag aagtgtttcc    1200
agactgaaaa ccctcttgaa tgccaagata aaggagaaga agaattacag aaatacatcc    1260
aggagagcca agcattggca aagcgaagct gcggcctctt ccagaaacta ggagaatatt    1320
acttacaaaa tgagtttctc gttgcttaca caaagaaagc cccccagctg acctcgtcgg    1380
agctgatggc catcaccaga aaaatggcag ccacagcagc cacttgttgc caactcagtg    1440
aggacaaact attggcctgt ggcgagggag cggctgacat tattatcgga cacttatgta    1500
tcagacatga aatgactcca gtaaacctg gtgttggcca gtgctgcact tcttcatatg    1560
ccaacaggag gccatgcttc agcagcttgg tggtggatga aacatatgtc cctcctgcat    1620
tctctgatga caagttcatt ttccataagg atctgtgcca agctcagggt gtagcgctgc    1680
```

-continued

```
aaaggatgaa gcaagagttt ctcattaacc ttgtgaagca aaagccacaa ataacagagg    1740
aacaacttga ggctctcatt gcagatttct caggcctgtt ggagaaatgc tgccaaggcc    1800
aggaacagga agtctgcttt gctgaagagg gacaaaaact gatttcaaaa actggtgctg    1860
ctttgggagt ttaaattact tcaggggaag agaagacaaa acgagtcttt cattcggtgt    1920
gaacttttct ctttaatttt aactgattta acacttttg tgaattaatg ataaagactt     1980
ttatgtgaga tttccttatc acagaaataa aatatctcca aa                       2022
```

<210> SEQ ID NO 2
<211> LENGTH: 590
<212> TYPE: PRT
<213> ORGANISM: Homo sapiens

<400> SEQUENCE: 2

```
Thr Leu His Arg Asn Glu Tyr Gly Ile Ala Ser Ile Leu Asp Ser Tyr
  1               5                  10                  15
Gln Cys Thr Ala Glu Ile Ser Leu Ala Asp Leu Ala Thr Ile Phe Phe
                 20                  25                  30
Ala Gln Phe Val Gln Glu Ala Thr Tyr Lys Glu Val Ser Lys Met Val
             35                  40                  45
Lys Asp Ala Leu Thr Ala Ile Glu Lys Pro Thr Gly Asp Glu Gln Ser
         50                  55                  60
Ser Gly Cys Leu Glu Asn Gln Leu Pro Ala Phe Leu Glu Glu Leu Cys
 65                  70                  75                  80
His Glu Lys Glu Ile Leu Glu Lys Tyr Gly His Ser Asp Cys Cys Ser
                 85                  90                  95
Gln Ser Glu Glu Gly Arg His Asn Cys Phe Leu Ala His Lys Lys Pro
                100                 105                 110
Thr Ala Ala Trp Ile Pro Leu Phe Gln Val Pro Glu Pro Val Thr Ser
            115                 120                 125
Cys Glu Ala Tyr Glu Glu Asp Arg Glu Thr Phe Met Asn Lys Phe Ile
        130                 135                 140
Tyr Glu Ile Ala Arg Arg His Pro Phe Leu Tyr Ala Pro Thr Ile Leu
145                 150                 155                 160
Leu Ser Ala Ala Gly Tyr Glu Lys Ile Ile Pro Ser Cys Cys Lys Ala
                165                 170                 175
Glu Asn Ala Val Glu Cys Phe Gln Thr Lys Ala Ala Thr Val Thr Lys
            180                 185                 190
Glu Leu Arg Glu Ser Ser Leu Leu Asn Gln His Ala Cys Pro Val Met
        195                 200                 205
Lys Asn Phe Gly Thr Arg Thr Phe Gln Ala Ile Thr Val Thr Lys Leu
    210                 215                 220
Ser Gln Lys Phe Thr Lys Val Asn Phe Thr Glu Ile Gln Lys Leu Val
225                 230                 235                 240
Leu Asp Val Ala His Val His Glu His Cys Cys Arg Ala Asp Val Leu
                245                 250                 255
Asp Cys Leu Gln Asp Gly Glu Lys Ile Met Ser Tyr Ile Cys Ser Gln
            260                 265                 270
Gln Asp Thr Leu Ser Asn Lys Ile Thr Glu Cys Cys Lys Leu Thr Thr
        275                 280                 285
Leu Glu Arg Gly Gln Cys Ile Ile His Ala Glu Asn Asp Glu Lys Pro
    290                 295                 300
Glu Gly Leu Ser Pro Asn Leu Asn Arg Phe Leu Gly Asp Arg Asp Phe
305                 310                 315                 320
Asn Gln Phe Ser Ser Gly Glu Lys Asn Ile Phe Leu Ala Ser Phe Val
                325                 330                 335
His Glu Tyr Ser Arg Arg His Pro Gln Leu Ala Val Ser Val Ile Leu
            340                 345                 350
Arg Val Ala Lys Gly Tyr Gln Glu Leu Leu Glu Lys Cys Phe Gln Thr
        355                 360                 365
Glu Asn Pro Leu Glu Cys Gln Asp Lys Gly Glu Glu Glu Leu Gln Lys
    370                 375                 380
Tyr Ile Gln Glu Ser Gln Ala Leu Ala Lys Arg Ser Cys Gly Leu Phe
385                 390                 395                 400
Gln Lys Leu Gly Glu Tyr Tyr Leu Gln Asn Glu Phe Leu Val Ala Tyr
                405                 410                 415
Thr Lys Lys Ala Pro Gln Leu Thr Ser Ser Glu Leu Met Ala Ile Thr
            420                 425                 430
Arg Lys Met Ala Ala Thr Ala Ala Thr Cys Cys Gln Leu Ser Glu Asp
        435                 440                 445
Lys Leu Leu Ala Cys Gly Glu Gly Ala Ala Asp Ile Ile Ile Gly His
    450                 455                 460
Leu Cys Ile Arg His Glu Met Thr Pro Val Asn Pro Gly Val Gly Gln
465                 470                 475                 480
Cys Cys Thr Ser Ser Tyr Ala Asn Arg Arg Pro Cys Phe Ser Ser Leu
                485                 490                 495
Val Val Asp Glu Thr Tyr Val Pro Pro Ala Phe Ser Asp Lys Phe
            500                 505                 510
```

```
Ile Phe His Lys Asp Leu Cys Gln Ala Gln Gly Val Ala Leu Gln Arg
            515                 520                 525
Met Lys Gln Glu Phe Leu Ile Asn Leu Val Lys Gln Lys Pro Gln Ile
        530                 535                 540
Thr Glu Glu Gln Leu Glu Ala Leu Ile Ala Asp Phe Ser Gly Leu Leu
545                 550                 555                 560
Glu Lys Cys Cys Gln Gly Gln Gln Glu Val Cys Phe Ala Glu Glu
                565                 570                 575
Gly Gln Lys Leu Ile Ser Lys Thr Gly Ala Ala Leu Gly Val
                580                 585                 590
```

<210> SEQ ID NO 3
<211> LENGTH: 197
<212> TYPE: PRT
<213> ORGANISM: Homo sapiens

<400> SEQUENCE: 3

```
Thr Leu His Arg Asn Glu Tyr Gly Ile Ala Ser Ile Leu Asp Ser Tyr
 1               5                   10                  15
Gln Cys Thr Ala Glu Ile Ser Leu Ala Asp Leu Ala Thr Ile Phe Phe
            20                  25                  30
Ala Gln Phe Val Gln Glu Ala Thr Tyr Lys Glu Val Ser Lys Met Val
        35                  40                  45
Lys Asp Ala Leu Thr Ala Ile Glu Lys Pro Thr Gly Asp Glu Gln Ser
    50                  55                  60
Ser Gly Cys Leu Glu Asn Gln Leu Pro Ala Phe Leu Glu Glu Leu Cys
65                  70                  75                  80
His Glu Lys Glu Ile Leu Glu Lys Tyr Gly His Ser Asp Cys Cys Ser
                85                  90                  95
Gln Ser Glu Glu Gly Arg His Asn Cys Phe Leu Ala His Lys Lys Pro
            100                 105                 110
Thr Ala Ala Trp Ile Pro Leu Phe Gln Val Pro Glu Pro Val Thr Ser
        115                 120                 125
Cys Glu Ala Tyr Glu Glu Asp Arg Glu Thr Phe Met Asn Lys Phe Ile
    130                 135                 140
Tyr Glu Ile Ala Arg Arg His Pro Phe Leu Tyr Ala Pro Thr Ile Leu
145                 150                 155                 160
Leu Ser Ala Ala Gly Tyr Glu Lys Ile Ile Pro Ser Cys Cys Lys Ala
                165                 170                 175
Glu Asn Ala Val Glu Cys Phe Gln Thr Lys Ala Ala Thr Val Thr Lys
            180                 185                 190
Glu Leu Arg Glu Ser
            195
```

<210> SEQ ID NO 4
<211> LENGTH: 192
<212> TYPE: PRT
<213> ORGANISM: Homo sapiens

<400> SEQUENCE: 4

```
Ser Leu Leu Asn Gln His Ala Cys Pro Val Met Lys Asn Phe Gly Thr
 1               5                   10                  15
Arg Thr Phe Gln Ala Ile Thr Val Thr Lys Leu Ser Gln Lys Phe Thr
            20                  25                  30
Lys Val Asn Phe Thr Glu Ile Gln Lys Leu Val Leu Asp Val Ala His
        35                  40                  45
Val His Glu His Cys Cys Arg Ala Asp Val Leu Asp Cys Leu Gln Asp
    50                  55                  60
Gly Glu Lys Ile Met Ser Tyr Ile Cys Ser Gln Gln Asp Thr Leu Ser
65                  70                  75                  80
Asn Lys Ile Thr Glu Cys Cys Lys Leu Thr Thr Leu Glu Arg Gly Gln
                85                  90                  95
Cys Ile Ile His Ala Glu Asn Asp Glu Lys Pro Glu Gly Leu Ser Pro
            100                 105                 110
Asn Leu Asn Arg Phe Leu Gly Asp Arg Asp Phe Asn Gln Phe Ser Ser
        115                 120                 125
Gly Glu Lys Asn Ile Phe Leu Ala Ser Phe Val His Glu Tyr Ser Arg
    130                 135                 140
Arg His Pro Gln Leu Ala Val Ser Val Ile Leu Arg Val Ala Lys Gly
145                 150                 155                 160
Tyr Gln Glu Leu Leu Glu Lys Cys Phe Gln Thr Glu Asn Pro Leu Glu
                165                 170                 175
Cys Gln Asp Lys Gly Glu Glu Leu Gln Lys Tyr Ile Gln Glu Ser
            180                 185                 190
```

```
<210> SEQ ID NO 5
<211> LENGTH: 201
<212> TYPE: PRT
<213> ORGANISM: Homo sapiens

<400> SEQUENCE: 5

Gln Ala Leu Ala Lys Arg Ser Cys Gly Leu Phe Gln Lys Leu Gly Glu
    1               5                   10                  15
    Tyr Tyr Leu Gln Asn Glu Phe Leu Val Ala Tyr Thr Lys Lys Ala Pro
                20                  25                  30
    Gln Leu Thr Ser Ser Glu Leu Met Ala Ile Thr Arg Lys Met Ala Ala
                    35                  40                  45
    Thr Ala Ala Thr Cys Cys Gln Leu Ser Glu Asp Lys Leu Leu Ala Cys
            50                  55                  60
    Gly Glu Gly Ala Ala Asp Ile Ile Ile Gly His Leu Cys Ile Arg His
    65                  70                  75                  80
    Glu Met Thr Pro Val Asn Pro Gly Val Gly Gln Cys Cys Thr Ser Ser
                    85                  90                  95
    Tyr Ala Asn Arg Arg Pro Cys Phe Ser Leu Val Val Asp Glu Thr
                100                 105                 110
    Tyr Val Pro Pro Ala Phe Ser Asp Asp Lys Phe Ile Phe His Lys Asp
                115                 120                 125
    Leu Cys Gln Ala Gln Gly Val Ala Leu Gln Arg Met Lys Gln Glu Phe
            130                 135                 140
    Leu Ile Asn Leu Val Lys Gln Lys Pro Gln Ile Thr Glu Glu Gln Leu
    145                 150                 155                 160
    Glu Ala Leu Ile Ala Asp Phe Ser Gly Leu Leu Glu Lys Cys Cys Gln
                    165                 170                 175
    Gly Gln Glu Gln Glu Val Cys Phe Ala Glu Glu Gly Gln Lys Leu Ile
                180                 185                 190
    Ser Lys Thr Gly Ala Ala Leu Gly Val
                195                 200

<210> SEQ ID NO 6
<211> LENGTH: 389
<212> TYPE: PRT
<213> ORGANISM: Homo sapiens

<400> SEQUENCE: 6

Thr Leu His Arg Asn Glu Tyr Gly Ile Ala Ser Ile Leu Asp Ser Tyr
    1               5                   10                  15
    Gln Cys Thr Ala Glu Ile Ser Leu Ala Asp Leu Ala Thr Ile Phe Phe
                20                  25                  30
    Ala Gln Phe Val Gln Glu Ala Thr Tyr Lys Glu Val Ser Lys Met Val
                    35                  40                  45
    Lys Asp Ala Leu Thr Ala Ile Glu Lys Pro Thr Gly Asp Glu Gln Ser
            50                  55                  60
    Ser Gly Cys Leu Glu Asn Gln Leu Pro Ala Phe Leu Glu Glu Leu Cys
    65                  70                  75                  80
    His Glu Lys Glu Ile Leu Glu Lys Tyr Gly His Ser Asp Cys Cys Ser
                    85                  90                  95
    Gln Ser Glu Glu Gly Arg His Asn Cys Phe Leu Ala His Lys Lys Pro
                100                 105                 110
    Thr Ala Ala Trp Ile Pro Leu Phe Gln Val Pro Glu Pro Val Thr Ser
            115                 120                 125
    Cys Glu Ala Tyr Glu Glu Asp Arg Glu Thr Phe Met Asn Lys Phe Ile
        130                 135                 140
    Tyr Glu Ile Ala Arg Arg His Pro Phe Leu Tyr Ala Pro Thr Ile Leu
    145                 150                 155                 160
    Leu Ser Ala Ala Gly Tyr Glu Lys Ile Ile Pro Ser Cys Cys Lys Ala
                    165                 170                 175
    Glu Asn Ala Val Glu Cys Phe Gln Thr Lys Ala Ala Thr Val Thr Lys
                180                 185                 190
    Glu Leu Arg Glu Ser Ser Leu Leu Asn Gln His Ala Cys Pro Val Met
            195                 200                 205
    Lys Asn Phe Gly Thr Arg Thr Phe Gln Ala Ile Thr Val Thr Lys Leu
        210                 215                 220
    Ser Gln Lys Phe Thr Lys Val Asn Phe Thr Glu Ile Gln Lys Leu Val
    225                 230                 235                 240
    Leu Asp Val Ala His Val His Glu His Cys Cys Arg Ala Asp Val Leu
                    245                 250                 255
    Asp Cys Leu Gln Asp Gly Glu Lys Ile Met Ser Tyr Ile Cys Ser Gln
                260                 265                 270
    Gln Asp Thr Leu Ser Asn Lys Ile Thr Glu Cys Cys Lys Leu Thr Thr
            275                 280                 285
```

```
     Leu Glu Arg Gly Gln Cys Ile Ile His Ala Glu Asn Asp Glu Lys Pro
         290                 295                 300
     Glu Gly Leu Ser Pro Asn Leu Asn Arg Phe Leu Gly Asp Arg Asp Phe
     305                 310                 315                 320
     Asn Gln Phe Ser Ser Gly Glu Lys Asn Ile Phe Leu Ala Ser Phe Val
                     325                 330                 335
     His Glu Tyr Ser Arg Arg His Pro Gln Leu Ala Val Ser Val Ile Leu
                 340                 345                 350
     Arg Val Ala Lys Gly Tyr Gln Glu Leu Leu Glu Lys Cys Phe Gln Thr
             355                 360                 365
     Glu Asn Pro Leu Glu Cys Gln Asp Lys Gly Glu Glu Glu Leu Gln Lys
         370                 375                 380
     Tyr Ile Gln Glu Ser
     385

<210> SEQ ID NO 7
<211> LENGTH: 393
<212> TYPE: PRT
<213> ORGANISM: Homo sapiens

<400> SEQUENCE: 7

Ser Leu Leu Asn Gln His Ala Cys Pro Val Met Lys Asn Phe Gly Thr
     1               5                   10                  15
     Arg Thr Phe Gln Ala Ile Thr Val Thr Lys Leu Ser Gln Lys Phe Thr
                     20                  25                  30
     Lys Val Asn Phe Thr Glu Ile Gln Lys Leu Val Leu Asp Val Ala His
                 35                  40                  45
     Val His Glu His Cys Cys Arg Ala Asp Val Leu Asp Cys Leu Gln Asp
             50                  55                  60
     Gly Glu Lys Ile Met Ser Tyr Ile Cys Ser Gln Asp Thr Leu Ser
     65                  70                  75                  80
     Asn Lys Ile Thr Glu Cys Cys Lys Leu Thr Thr Leu Glu Arg Gly Gln
                     85                  90                  95
     Cys Ile Ile His Ala Glu Asn Asp Glu Lys Pro Glu Gly Leu Ser Pro
                 100                 105                 110
     Asn Leu Asn Arg Phe Leu Gly Asp Arg Asp Phe Asn Gln Phe Ser Ser
             115                 120                 125
     Gly Glu Lys Asn Ile Phe Leu Ala Ser Phe Val His Glu Tyr Ser Arg
     130                 135                 140
     Arg His Pro Gln Leu Ala Val Ser Val Ile Leu Arg Val Ala Lys Gly
     145                 150                 155                 160
     Tyr Gln Glu Leu Leu Glu Lys Cys Phe Gln Thr Glu Asn Pro Leu Glu
                     165                 170                 175
     Cys Gln Asp Lys Gly Glu Glu Glu Leu Gln Lys Tyr Ile Gln Glu Ser
                 180                 185                 190
     Gln Ala Leu Ala Lys Arg Ser Cys Gly Leu Phe Gln Lys Leu Gly Glu
             195                 200                 205
     Tyr Tyr Leu Gln Asn Glu Phe Leu Val Ala Tyr Thr Lys Lys Ala Pro
     210                 215                 220
     Gln Leu Thr Ser Ser Glu Leu Met Ala Ile Thr Arg Lys Met Ala Ala
     225                 230                 235                 240
     Thr Ala Ala Thr Cys Cys Gln Leu Ser Glu Asp Lys Leu Leu Ala Cys
                     245                 250                 255
     Gly Glu Gly Ala Ala Asp Ile Ile Ile Gly His Leu Cys Ile Arg His
                 260                 265                 270
     Glu Met Thr Pro Val Asn Pro Gly Val Gly Gln Cys Cys Thr Ser Ser
             275                 280                 285
     Tyr Ala Asn Arg Arg Pro Cys Phe Ser Ser Leu Val Val Asp Glu Thr
     290                 295                 300
     Tyr Val Pro Pro Ala Phe Ser Asp Asp Lys Phe Ile Phe His Lys Asp
     305                 310                 315                 320
     Leu Cys Gln Ala Gln Gly Val Ala Leu Gln Arg Met Lys Gln Glu Phe
                     325                 330                 335
     Leu Ile Asn Leu Val Lys Gln Lys Pro Gln Ile Thr Glu Glu Gln Leu
                 340                 345                 350
     Glu Ala Leu Ile Ala Asp Phe Ser Gly Leu Leu Glu Lys Cys Cys Gln
             355                 360                 365
     Gly Gln Glu Gln Glu Val Cys Phe Ala Glu Glu Gly Gln Lys Leu Ile
     370                 375                 380
     Ser Lys Thr Gly Ala Ala Leu Gly Val
     385                 390

<210> SEQ ID NO 8
<211> LENGTH: 325
<212> TYPE: PRT
<213> ORGANISM: Homo sapiens
```

<400> SEQUENCE: 8

| | | | | | | | | | | | | | | | |
|---|---|---|---|---|---|---|---|---|---|---|---|---|---|---|---|
|Met|Ser|Tyr|Ile|Cys|Ser|Gln|Gln|Asp|Thr|Leu|Ser|Asn|Lys|Ile|Thr|
|1| | | |5| | | | |10| | | | |15| |
|Glu|Cys|Cys|Lys|Leu|Thr|Thr|Leu|Glu|Arg|Gly|Gln|Cys|Ile|Ile|His|
| | | | |20| | | | |25| | | | |30| |
|Ala|Glu|Asn|Asp|Glu|Lys|Pro|Glu|Gly|Leu|Ser|Pro|Asn|Leu|Asn|Arg|
| | | | |35| | | | |40| | | | |45| |
|Phe|Leu|Gly|Asp|Arg|Asp|Phe|Asn|Gln|Phe|Ser|Ser|Gly|Glu|Lys|Asn|
| |50| | | | |55| | | | |60| | | | |
|Ile|Phe|Leu|Ala|Ser|Phe|Val|His|Glu|Tyr|Ser|Arg|Arg|His|Pro|Gln|
|65| | | | |70| | | | |75| | | | |80|
|Leu|Ala|Val|Ser|Val|Ile|Leu|Arg|Val|Ala|Lys|Gly|Tyr|Gln|Glu|Leu|
| | | | |85| | | | |90| | | | |95| |
|Leu|Glu|Lys|Cys|Phe|Gln|Thr|Glu|Asn|Pro|Leu|Glu|Cys|Gln|Asp|Lys|
| | | | |100| | | | |105| | | | |110| |
|Gly|Glu|Glu|Glu|Leu|Gln|Lys|Tyr|Ile|Gln|Glu|Ser|Gln|Ala|Leu|Ala|
| | | | |115| | | | |120| | | | |125| |
|Lys|Arg|Ser|Cys|Gly|Leu|Phe|Gln|Lys|Leu|Gly|Glu|Tyr|Tyr|Leu|Gln|
| | | | |130| | | | |135| | | | |140| |
|Asn|Glu|Phe|Leu|Val|Ala|Tyr|Thr|Lys|Lys|Ala|Pro|Gln|Leu|Thr|Ser|
|145| | | | |150| | | | |155| | | | |160|
|Ser|Glu|Leu|Met|Ala|Ile|Thr|Arg|Lys|Met|Ala|Ala|Thr|Ala|Ala|Thr|
| | | | |165| | | | |170| | | | |175| |
|Cys|Cys|Gln|Leu|Ser|Glu|Asp|Lys|Leu|Leu|Ala|Cys|Gly|Glu|Gly|Ala|
| | | | |180| | | | |185| | | | |190| |
|Ala|Asp|Ile|Ile|Gly|His|Leu|Cys|Ile|Arg|His|Glu|Met|Thr|Pro|
| | | | |195| | | | |200| | | | |205| |
|Val|Asn|Pro|Gly|Val|Gly|Gln|Cys|Cys|Thr|Ser|Ser|Tyr|Ala|Asn|Arg|
| | | | |210| | | | |215| | | | |220| |
|Arg|Pro|Cys|Phe|Ser|Ser|Leu|Val|Val|Asp|Glu|Thr|Tyr|Val|Pro|Pro|
|225| | | | |230| | | | |235| | | | |240|
|Ala|Phe|Ser|Asp|Asp|Lys|Phe|Ile|Phe|His|Lys|Asp|Leu|Cys|Gln|Ala|
| | | | |245| | | | |250| | | | |255| |
|Gln|Gly|Val|Ala|Leu|Gln|Arg|Met|Lys|Gln|Glu|Phe|Leu|Ile|Asn|Leu|
| | | | |260| | | | |265| | | | |270| |
|Val|Lys|Gln|Lys|Pro|Gln|Ile|Thr|Glu|Glu|Gln|Leu|Glu|Ala|Leu|Ile|
| | | | |275| | | | |280| | | | |285| |
|Ala|Asp|Phe|Ser|Gly|Leu|Leu|Glu|Lys|Cys|Cys|Gln|Gly|Gln|Glu|Gln|
| | | | |290| | | | |295| | | | |300| |
|Glu|Val|Cys|Phe|Ala|Glu|Glu|Gly|Gln|Lys|Leu|Ile|Ser|Lys|Thr|Gly|
|305| | | | |310| | | | |315| | | | |320|
|Ala|Ala|Leu|Gly|Val| | | | | | | | | | | |
| | | | |325| | | | | | | | | | | |

<210> SEQ ID NO 9
<211> LENGTH: 30
<212> TYPE: DNA
<213> ORGANISM: Homo sapiens

<400> SEQUENCE: 9

```
aaaaaaggta ccacactgca tagaaatgaa                                30
```

<210> SEQ ID NO 10
<211> LENGTH: 33
<212> TYPE: DNA
<213> ORGANISM: Homo sapiens

<400> SEQUENCE: 10

```
aaaaaaggat ccttagcttt ctcttaattc ttt                            33
```

<210> SEQ ID NO 11
<211> LENGTH: 33
<212> TYPE: DNA
<213> ORGANISM: Homo sapiens

<400> SEQUENCE: 11

```
aaaaaaatcg atatgagctt gttaaatcaa cat                            33
```

<210> SEQ ID NO 12
<211> LENGTH: 33

```
<212> TYPE: DNA
<213> ORGANISM: Homo sapiens

<400> SEQUENCE: 12
aaaaaaggat ccttagctct cctggatgta ttt                            33

<210> SEQ ID NO 13
<211> LENGTH: 33
<212> TYPE: DNA
<213> ORGANISM: Homo sapiens

<400> SEQUENCE: 13
aaaaaaatcg atatgcaagc attggcaaag cga                            33

<210> SEQ ID NO 14
<211> LENGTH: 33
<212> TYPE: DNA
<213> ORGANISM: Homo sapiens

<400> SEQUENCE: 14
aaaaaaggat ccttaaactc ccaaagcagc acg                            33

<210> SEQ ID NO 15
<211> LENGTH: 33
<212> TYPE: DNA
<213> ORGANISM: Homo sapiens

<400> SEQUENCE: 15
aaaaaaatcg atatgtccta catatgttct caa                            33

<210> SEQ ID NO 16
<211> LENGTH: 9
<212> TYPE: PRT
<213> ORGANISM: Homo sapiens

<400> SEQUENCE: 16

Ser Tyr Ile Cys Ser Gln Gln Asp Thr
     1               5
```